(12) United States Patent
Zhu et al.

(10) Patent No.: US 10,370,334 B2
(45) Date of Patent: Aug. 6, 2019

(54) INOSITOL NICOTINATE CRYSTALLINE FORM A AND PREPARATION METHOD THEREFOR

(71) Applicant: WEIFANG SHENGYU PHARMA CO., LTD., Weifang, Shandong (CN)

(72) Inventors: Liwei Zhu, Shandong (CN); Xuefeng Mei, Sandong (CN); Jianrong Wang, Sandong (CN)

(73) Assignee: WEIFANG SHENGYU PHARMA CO., LTD., Weifang, Shandong (CN)

( * ) Notice: Subject to any disclaimer, the term of this patent is extended or adjusted under 35 U.S.C. 154(b) by 0 days.

(21) Appl. No.: 15/762,849

(22) PCT Filed: Sep. 21, 2016

(86) PCT No.: PCT/CN2016/099643
§ 371 (c)(1),
(2) Date: Mar. 23, 2018

(87) PCT Pub. No.: WO2017/050241
PCT Pub. Date: Mar. 30, 2017

(65) Prior Publication Data
US 2018/0273480 A1 Sep. 27, 2018

(30) Foreign Application Priority Data

Sep. 23, 2015 (CN) .......................... 2015 1 0613142

(51) Int. Cl.
*B01D 9/00* (2006.01)
*A61K 31/455* (2006.01)
(Continued)

(52) U.S. Cl.
CPC ......... *C07D 213/80* (2013.01); *B01D 9/0031* (2013.01); *B01D 9/0054* (2013.01);
(Continued)

(58) Field of Classification Search
CPC .. C07D 213/80; B01D 9/0031; B01D 9/0054; B01D 9/0063; A61K 31/455
(Continued)

(56) References Cited

U.S. PATENT DOCUMENTS 4,801,597 A 1/1989 Stacpoole et al.

FOREIGN PATENT DOCUMENTS

CN 102627601 A 8/2012
WO 1985005362 A1 12/1985

OTHER PUBLICATIONS

Badgett; J. Am. Chem. Soc., 1947, 69, 2907. (Year: 1947).*
(Continued)

*Primary Examiner* — Daniel R Carcanague
(74) *Attorney, Agent, or Firm* — Novick, Kim & Lee, PLLC; Bin Lu

(57) ABSTRACT

Provided are an inositol nicotinate crystalline form A and a preparation method therefor. The X-ray powder diffraction analysis, obtained by using Cu-Kα ray measurement, of the inositol nicotinate crystalline form A has obvious characteristic diffraction peaks at least at 2θ values, expressed in degrees, of 7.05, 7.41, 9.74, 17.80, 19.86, 23.57, 25.48 and 26.20 with an error range of +/−0.2°. The preparation method is one of or a mixed crystallization method of two or more of an evaporation crystallization method, a cooling crystallization method or an anti-solvent crystallization method. The process thereof is simple and easy to operate, and has more selectivity; the inositol nicotinate crystalline form A can be prepared by various methods, and the prepared product has a good crystallization degree and high chemical stability; and the inositol nicotinate crystalline form A prepared by the present method does not have the problem that a residual solvent is out-of-limit.

17 Claims, 3 Drawing Sheets

(51) Int. Cl.
*C07D 213/80* (2006.01)
*C07D 213/803* (2006.01)

(52) U.S. Cl.
CPC ....... *B01D 9/0063* (2013.01); *C07D 213/803* (2013.01); *A61K 31/455* (2013.01)

(58) Field of Classification Search
USPC ........................................................ 546/322
See application file for complete search history.

(56) References Cited

OTHER PUBLICATIONS

Feng Liang et al., "Synthesis of inositol hexanicotinate", Applied Chemical Industry, Jun. 2001, vol. 30, No. 3, pp. 19-20 (English abstract on p. 20).

* cited by examiner

INOSITOL NICOTINATE CRYSTALLINE FORM A AND PREPARATION METHOD THEREFOR

TECHNICAL FIELD

The present invention relates to the technical field of chemical drugs, in particular to inositol nicotinate crystalline form A and preparation method therefor.

BACKGROUND

Polymorphism refers to such a phenomenon that solid states with different physicochemical properties formed by solid substances in two or more different spatial arrangements. In the field of drug research, polymorphs also include multi-component crystal forms, such as organic solvates and hydrates. Crystalline research and control are important research contents in drug development.

Inositol Nicotinate, chemically named cis-1,2,3,5-trans-4,6-cyclohexanehexol niacinate, is a mild peripheral vasodilator, after absorption, it is gradually hydrolyzed into nicotinic acid and inositol in vivo, and it has the pharmacological effects of both niacin and inositol. Its vasodilating effect is milder and longer lasting than niacin, and it can selectively expand blood vessels in lesions and sensitive areas that are stimulated by cold, while the expansion for the normal blood vessels is weaker. In addition, it also has the effects of thrombolysis, anticoagulation, anti-fatty liver, and reduction of capillary fragility, without the side effects such as flushing and stomach discomfort after taking niacin. Clinically, inositol nicotinic acid ester tablets are mainly used for auxiliary treatment of hyperlipidemia, atherosclerosis, and various peripheral vascular disorders (such as occlusive arteriosclerosis, acra arterial spasm, frostbite, vascular migraine, etc.)

The structure of inositol nicotinate is as shown below:

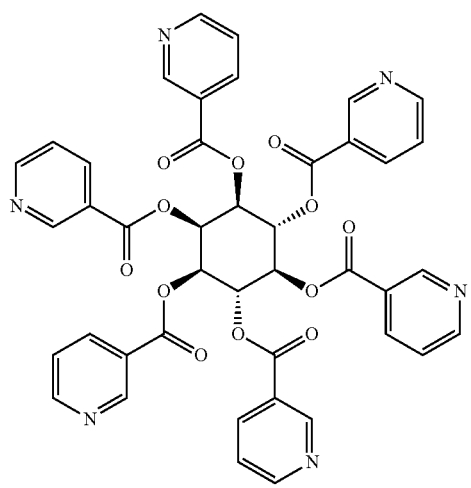 [SMILES: O=C(O[C@H]1[C@H](OC(=O)c2cccnc2)[C@@H](OC(=O)c2cccnc2)[C@H](OC(=O)c2cccnc2)[C@@H](OC(=O)c2cccnc2)[C@H]1OC(=O)c1cccnc1)c1cccnc1]

Inositol nicotinate is only soluble in hot dimethylformamide or dimethyl sulfoxide. It is very slightly soluble in chloroform and insoluble in water, ethanol and other organic solvents. No crystal form has been reported for this compound. The synthesis of inositol nicotinate is generally obtained by the condensation of inositol and nicotinic acid using pyridine as a solvent. Due to poor solubility, product purification and removal of residual pyridine are extremely difficult, while as high boiling point solvents, the use of dimethylformamide or dimethyl sulfoxide in crystallization and purification can also lead to the excessive residue of the solvent of dimethylformamide or dimethyl sulfoxide.

SUMMARY OF INVENTION

In the first aspect of the present invention, an inositol nicotinate crystal form A having good crystallinity and high chemical stability is provided.

To solve the above mentioned technical problem, the technical solution of the present invention is: an inositol nicotinate crystal form A, the X-ray powder diffraction analysis of the crystal form A is obtained using Cu-Kα ray measurement, of which the diffraction peak has the following characteristics:

| 2θ(±0.2°) | d(Å) | Relative intensitiy (%) |
|---|---|---|
| 7.05 | 12.53 | 23.4 |
| 7.41 | 11.92 | 46.1 |
| 9.74 | 9.08 | 23.3 |
| 10.16 | 8.70 | 4.3 |
| 11.26 | 7.85 | 8.7 |
| 12.75 | 7.04 | 3.6 |
| 13.66 | 6.48 | 9.2 |
| 17.04 | 5.20 | 12.9 |
| 17.80 | 4.98 | 100 |
| 18.36 | 4.83 | 17.3 |
| 19.28 | 4.60 | 16.2 |
| 19.86 | 4.47 | 24.3 |
| 20.62 | 4.30 | 5.0 |
| 20.97 | 4.23 | 14.9 |
| 21.29 | 4.17 | 8.6 |
| 21.58 | 4.11 | 15.5 |
| 22.03 | 4.03 | 9.0 |
| 22.23 | 3.99 | 16.8 |
| 22.45 | 3.95 | 12.5 |
| 23.57 | 3.77 | 20.4 |
| 23.93 | 3.71 | 11.0 |
| 25.2 | 3.53 | 11.9 |
| 25.48 | 3.49 | 33.9 |
| 26.20 | 3.40 | 26.1 |
| 26.58 | 3.35 | 9.0. |

In another preferred embodiment, X-ray powder diffraction analysis obtained using Cu-Kα ray measurement has an obvious characteristic diffraction peak 2θ value at least at 7.05, 7.41, 9.74, 17.80, 19.86, 23.57, 25.48 and 26.20 expressed as degrees, with an error range of ±0.2°.

In another preferred embodiment, X-ray powder diffraction of crystal form A expressed as 2θ value degrees has an obvious characteristic diffraction peak at diffraction angles of 7.05, 7.41, 9.74, 10.16, 11.26, 12.75, 17.80, 19.86, 20.97, 23.57, 25.48 and 26.20, 26.58, with an error range of ±0.2°.

In another preferred embodiment, the X-ray powder diffraction pattern of the crystal form A is essentially as shown in FIG. 1.

In another preferred embodiment, the crystal form A belongs to a monoclinic system, of which the spatial point group is P21/c, and the unit cell parameters of which are: a=12.0470(2) Å, b=17.4688(3)Å, c=18.3057(3)Å; α=γ=90.00°, β=94.5170(10°); the unit cell volume of which is 3840.41 Å$^3$, the crystal density of which is 1.4022 g/cm$^3$.

In another preferred embodiment, the differential scanning calorimetry analysis of crystal form A starts melting at 260° C., and has a maximum endothermic melting peak at 261.14° C.

In another preferred embodiment, the differential scanning calorimetry pattern of the crystal form A is essentially as shown in FIG. 2.

In another preferred embodiment, the thermogravimetic analysis pattern of the crystal form A is essentially as shown in FIG. 3.

In another preferred embodiment, for the thermogravimetic analysis, the crystal form A has a decomposition temperature of 300±1° C., and there is no weight loss peak of crystal water or a binding solvent before the decomposition temperature.

In another preferred embodiment, the Raman spectrum of the crystal form A has obvious characteristic peaks at least at 622 cm$^{-1}$, 827 cm$^{-1}$, 903 cm$^{-1}$, 1033 cm$^{-1}$, 1194 cm$^{-1}$, 1276 cm$^{-1}$, 1302 cm$^{-1}$, 1387 cm$^{-1}$, 1592 cm$^{-1}$, 1720 cm$^{-1}$, 1741 cm$^{-1}$, 2971 cm$^{-1}$, and 3067 cm$^{-1}$, with an error range of ±2 cm$^{-1}$.

In another preferred embodiment, the Raman spectrum of the crystal form A is as essentially shown in FIG. 4.

In another preferred embodiment, the crystal form A is anhydrate.

In the second aspect of the present invention, a preparation method of inositol niacinate crystal form A of which the process is simple, easy to operate, of which the product is of good crystallinity and high stability is provided, wherein comprising the steps:

(1) providing a mixture of nicotinyl nicotinate and solvent S, the solvent S includes haloalkane, alcohol, water, or combinations thereof, and the feed liquid ratio of the inositol nicotinate and the solvent S is 1 g: 5 mL to 1 g: 15 mL;

(2) Performing crystallization at room temperature to obtain the inositol nicotinate crystal form A.

In another preferred embodiment, the step (2) comprises: heating the mixture to 60-100° C., and optionally, cooling to 0-30° C., performing crystallization to obtain the inositol nicotinate crystal form A.

In another preferred embodiment, the step (2) comprises: adding an anti-solvent to the mixture described in step (1) at room temperature for the crystallization, thereby obtaining the inositol nicotinate crystal form A.

In another preferred embodiment, the step (2) comprises: adding an anti-solvent dropwise to the mixture described in step (1), heating the mixture to 25-70° C. to evaporate and crystallize, and thereby obtaining the inositol nicotinate crystal form A.

In another preferred embodiment, the step (2) further includes a filtering, washing and drying step.

To solve the above mentioned technical problem, the technical solution of the present invention is:

The preparation method is the evaporative crystallization method, the cooling crystallization method or the anti-solvent crystallization method, or a mixed crystallization method comprising at least two of the evaporative crystallization method, the cooling crystallization method and the anti-solvent crystallization method.

In another preferred embodiment, the evaporative crystallization method comprises the following steps: inositol nicotinate is dissolved in a mixed solvent of alkyl halide and alcohol, or a mixed solvent of alkyl halide and alcohol water, and placed at room temperature, or heated to volatilize or evaporate the alkyl halide in the system until solid crystals are precipitated, filtered, washed, dried to obtain.

In another preferred embodiment, the cooling crystallization method comprises the following steps: inositol nicotinate is dissolved in a mixed solvent of alkyl halide and alcohol, or a mixed solvent of alkyl halide with alcohol in water, heat to dissolve, and then cooling to precipitate solid crystals, filter, wash and dry to obtain.

In another preferred embodiment, the anti-solvent crystallization method comprises the following steps: inositol nicotinate is dissolved in a mixed solvent of alkyl halide and alcohol or a mixed solvent, of alkyl halide with alcohol in water, and an alcohol solvent is added dropwise at room temperature to precipitate solid crystals, filter, wash and dry to obtain.

In another preferred embodiment, the mixed crystallization method comprises the following steps: inositol nicotinate is dissolved in a mixed solvent of alkyl halide and alcohol, or a mixed solvent of alkyl halide with alcohol in water, evaporate the alkyl halide by heating while adding an alcohol solvent dropwise to the reaction liquid to precipitate the solid crystals, filter, wash, and dry to obtain.

In another preferred embodiment, the haloalkane is one or more of chloroform, dichloromethane, or dichloroethane.

In another preferred embodiment, the alcohol is one or two or more of methanol, ethanol or isopropanol.

In another preferred embodiment, the alcohol water is a mixed solvent of one or more of methanol, ethanol or isopropanol and water.

In another preferred embodiment, the anti-solvent is selected from the group consisting of: methanol, ethanol, isopropanol, water, and a combination thereof.

In another preferred embodiment, in a mixed solvent of alkyl halide and alcohol, the volume ratio of the halogenated hydrocarbon to the alcohol is 10:1 to 1:10, preferably 4:1 to 1:1.

In another preferred embodiment, the volume ratio of the solvent S and the anti-solvent is 10:1 to 1:1.

In another preferred embodiment, the drying is air blowing drying or vacuum drying, and the drying temperature is from room temperature to 110° C., preferably 80° C. to 100° C.

In the third aspect of the present invention, a use of the inositol nicotinate crystal form A for the preparation of a medicament and a feed is provided.

In the fourth aspect of the present invention, a pharmaceutical composition is provided, which comprises (a) the crystal form A according to the first aspect of the present invention, and (b) a pharmacologically acceptable carrier.

In the fifth aspect of the present invention, a method for treatment is provided, comprising the step of: administrating the inositol nicotinate crystal form A according to the first aspect of the present invention to a subject in need.

Due to the adoption of the above technical solution, the beneficial effects of the present invention are:

The preparation method of inositol nicotinate crystal form A provided by the present invention has the advantages of simple processing, easy operation, and more choices. The crystal form A of inositol nicotinate can be prepared by various methods, and the obtained product has a good crystallinity, high chemical stability, and there is no problem of solvent residue or excessive solvent in the crystal form A of inositol nicotinate prepared by the method of the present invention.

DETAILED DESCRIPTION

Figure 1:
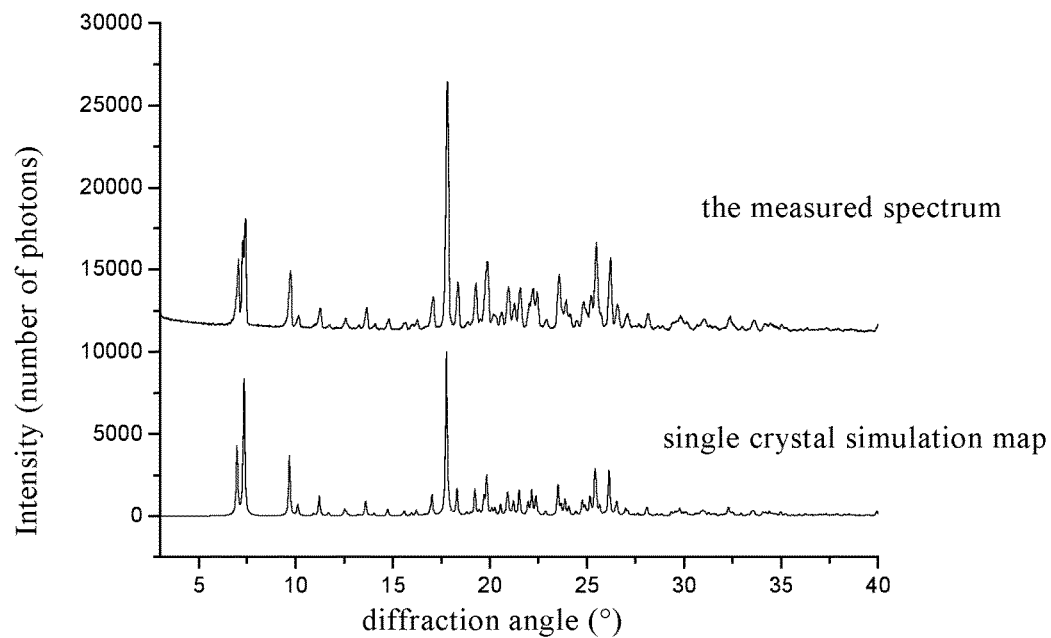
FIG. 1 is an X-ray powder diffraction (XRPD) pattern and a single crystal simulated powder diffraction pattern of crystal form A of inositol nicotinate provided by the present invention.

In order to make the objectives, technical solutions and advantages of the present invention more comprehensible, the present invention is further described in detail below with reference to the accompanying drawings and embodiments. It should be understood that the specific embodiments described herein are only used to explain the present invention, and are not intended to limit the present invention.

Regarding to the crystal form A of the present invention, an X-ray powder diffraction expressed at 2θ angle is represented by the form of a characteristic peak±x° at the diffraction angle peak, wherein x≤0.2, and preferably, x is 0.05, 0.1, or 0.2.

Description of Terms
Pharmaceutical Composition

A pharmaceutical composition is provided by the present invention, which comprises (a) the crystal form A according to the first aspect of the present invention, and (b) a pharmaceutically acceptable carrier.

The "active ingredient" in the pharmaceutical composition of the present invention refers to the crystal form A of inositol niacinate of the present invention.

"Safe and effective dosage" refers to the amount of the active ingredient which is enough to improve the patient's condition without any serious side effect.

Generally, the pharmaceutical composition contains 1-2000 mg active ingredient per dose, preferably, 10-200 mg active ingredient per dose. Preferably, "per dose" means one tablet or injection.

"Pharmaceutically acceptable carrier" means one or more compatible solid or liquid fillers or gel materials, which are suitable for human, and must have sufficient purity and sufficiently low toxicity.

"Compatibility" herein means that each component in the composition can be blended with the active ingredient of the invention and with each other, and would not significantly reduce the efficacy of the active ingredient.

Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the active ingredient or pharmaceutical compositions of the present invention, and the representative administration mode includes (but is not limited to): oral, intratumoral, rectal, parenteral (intravenous, intramuscular or subcutaneous) and so on.

Solid dosage forms for oral administration include capsules, tablets, pills, powders and granules.

The solid dosage forms can further be prepared by using coating and shell materials, such as enteric coatings and any other materials known in the art, and can comprise an opaque agent. The release of the active ingredient in the composition can be released in a delayed mode in a certain portion of the digestive tract. Examples of the embedding components include polymers and waxes.

Liquid dosage forms for oral administration include pharmaceutically acceptable emulsions, solutions, suspensions, syrups or tinctures. In addition to the active ingredients, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof. Besides these inert diluents, the composition may also contain additives such as wetting agents, emulsifiers, and suspending agent, sweetener, flavoring agents and perfume.

In addition to the active ingredients, the suspension may contain suspending agent, for example, ethoxylated isooctadecanol, polyoxyethylene sorbitol and sorbitan esters, microcrystalline cellulose, methanol aluminum and agar, or the combinations thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

When the pharmaceutical compositions are used, a safe and effective amount of the compounds of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the specific dose should also depend on various factors, such as the route of administration, patient healthy status, which are well within the skills of an experienced physician.

The compounds of the present invention may be administered alone or in combination with other therapeutic agents.

Detection Method

XRD (X-ray powder diffraction) method: instrument model: Bruker D8 advance

TG (Thermogravimetric Analysis) method: instrument model: Netzsch TG 209F3

DSC (differential scanning calorimetry) method: Perkin Elmer DSC 1200

DVS method: SMS DVS Intrinsic

Raw Material

The raw material inositol nicotinate used in the example of the present invention is purchased from Weifang Shengyu Pharmaceutical Co., Ltd.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

In the following examples, the unit of solid-liquid ratio is g (solid):mL (liquid).

Example 1

1 g of inositol niacinate crude was dissolved in 10 mL of a mixed solvent of methylene chloride/methanol (10/1, v/v), placed for 2 to 3 days at room temperature, spontaneously volatilized, and crystals were precipitated and filtered until the solvent volume was 0.5 mL, and the crystals were dried under vacuum at room temperature to give a 0.9 g of inositol nicotinate with high purity.

Example 2

30 g of inositol niacinate crude was added into 150 mL of a mixed solvent of chloroform/ethanol (4/1, v/v), stirred at room temperature for 1-2 h to be completely dissolved. 15 mL of 95% ethanol was added dropwise to the above reaction solution, after the addition, the mixture was stirred for 2 to 3 hours to precipitate a white solid, which was filtered, washed, and dried by blowing air at 100° C. for 1 hour to give a 24 g of inositol nicotinate crystal, which was the same with that in Example 1 through the identification by powder X-ray diffraction.

Example 3

30 g of inositol nicotinate crude was added into a mixed solvent of 120 mL of dichloroethane/isopropanol (1/1, v/v), heated to 60° C. to dissolve completely, and then cooled to 0-5° C. The crystals were precipitated, filtered, washed, and dried by blowing air at 110° C. for 1 h to give a 25 g of a white solid, which was the same with that in Example 1 through the identification by powder X-ray diffraction.

Example 4

100 g of inositol nicotinate crude was dissolved in 500 mL of a mixed solvent of dichloromethane/95% ethanol (4/1, v/v), and slowly added dropwise to 400 mL, 95% ethanol preheated to 70° C., the heating temperature and the dropping rate were controlled so that the dropping rate of the mixed solvent is basically the same as that of the distillation rate. After the dropwise addition is completed, some of the ethanol is further distilled off after the temperature was elevated, cooled to room temperature, filtered, washed with 95% ethanol, and dried by blowing air under 80° C. for 3 hours to give 98 g, which was the same crystal form with that in Example 1 through the identification by powder X-ray diffraction.

X-Ray Powder Diffraction Analysis (XRPD), differential scanning calorimetry (DSC), thermogravimetric analysis (TG), Raman spectroscopy (Raman) were performed on crystal form A of inositol nicotinate prepared in the above examples.

XRPD analysis: It was detected at room temperature using a Bruker D8 advance type diffractometer from German Brook Instrument Co., Ltd by Cu-Kα rays (λ=1.5418 Å), with a 2θ angle scanning from 3° to 40°, and the scanning speed was 0.2°/second.

Through the powder X-ray diffraction analysis, there are characteristic peaks at 7.05, 7.41, 9.74, 10.16, 11.26, 12.75, 13.66, 17.04, 17.80, 18.36, 19.28, 19.86, 20.62, 20.97, 21.58, 22.03, 23.57, 23.93, 25.20, 25.48, 26.20 and 26.58±0.2° etc expressed as 2θ reflection angle.

Additional crystallographic information is obtained from single crystal X-ray diffraction, the crystal is orthorhombic crystal, the symmetry space group is P21/c, and the unit cell parameters are: a=12.0470(2) Å, B=17.4688(3)Å, c=18.3057(3)Å; α=γ=90.00°, β=94.5170(10°); unit cell volume is 3840.41 Å$^3$ and crystal density is 1.4022 g/cm$^3$. There is no binding solvent in the crystal structure, and the powder diffraction pattern simulated by the single crystal diffraction is completely consistent with the experimentally measured powder X-ray diffraction pattern. The analysis result is shown in FIG. 1, indicating that crystal form A of inositol nicotinate obtained in the above examples has a good crystallinity.

Figure 2:
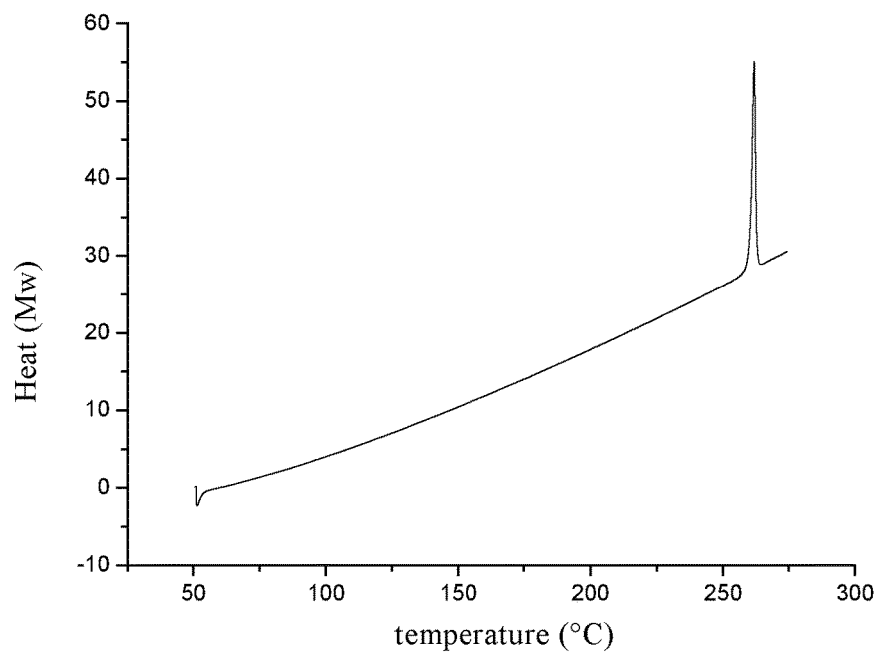
FIG. 2 is a differential scanning calorimetry (DSC) pattern of crystal form A of inositol nicotinate provided by the present invention.

DSC analysis: It was detected using a DSC 8500 differential scanning calorimeter from American Perkin Elmer Corporation, with a nitrogen atmosphere and a heating rate of 10° C./minute. The analysis results are shown in FIG. 2.

Figure 3:
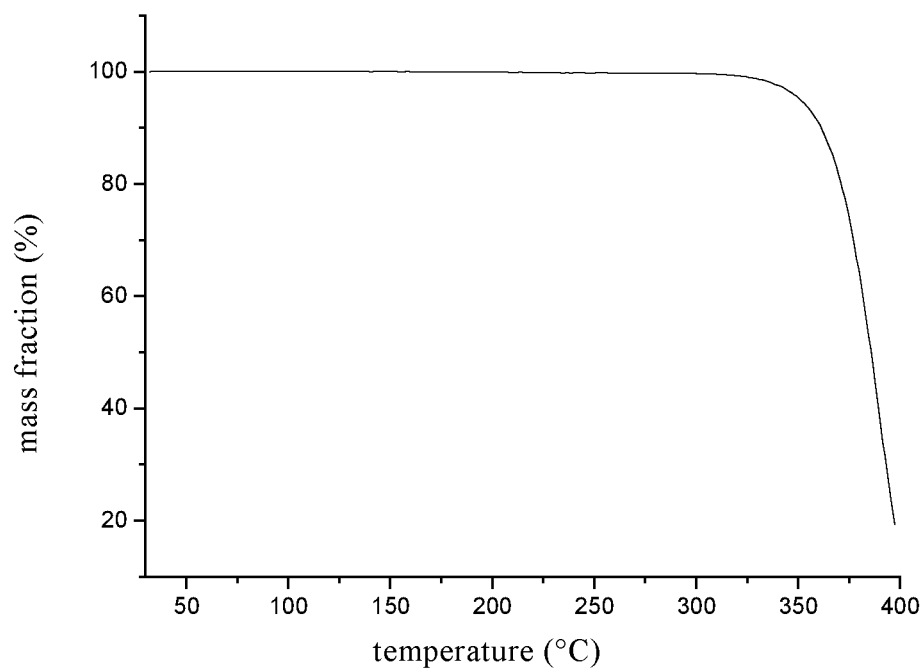
FIG. 3 is a thermogravimetric analysis (TG) pattern of crystal form A of inositol nicotinate provided by the present invention.

TG analysis: It was tested with a Netzsch TG 209F3 thermogravimetric analyzer from the German Nachi company, with a temperature range of 30-400° C., a scan rate of 10 K/min, and a purge gas of 25 mL/min. The analysis results are shown in FIG. 3.

Figure 4:
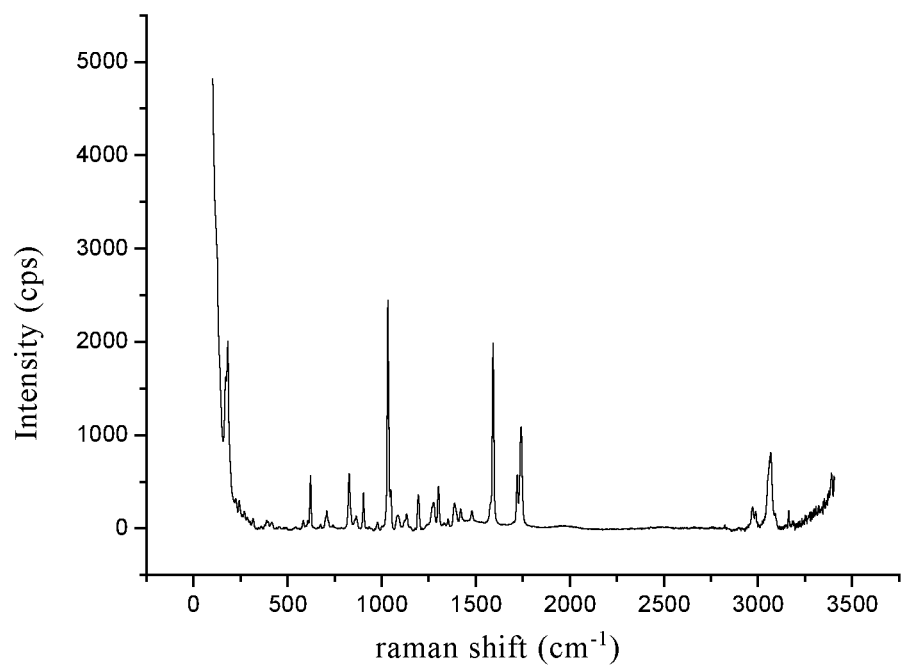
FIG. 4 is a Raman spectrogram of crystal form A of inositol nicotinate provided by the present invention.

Raman spectroscopic analysis: It was detected at room temperature using a DXR Micro-Raman spectrometer from Thermo Electron Corporation, with a detection range of 3500-50 cm' Raman shift. The analysis results are shown in FIG. 4.

Figure 5:
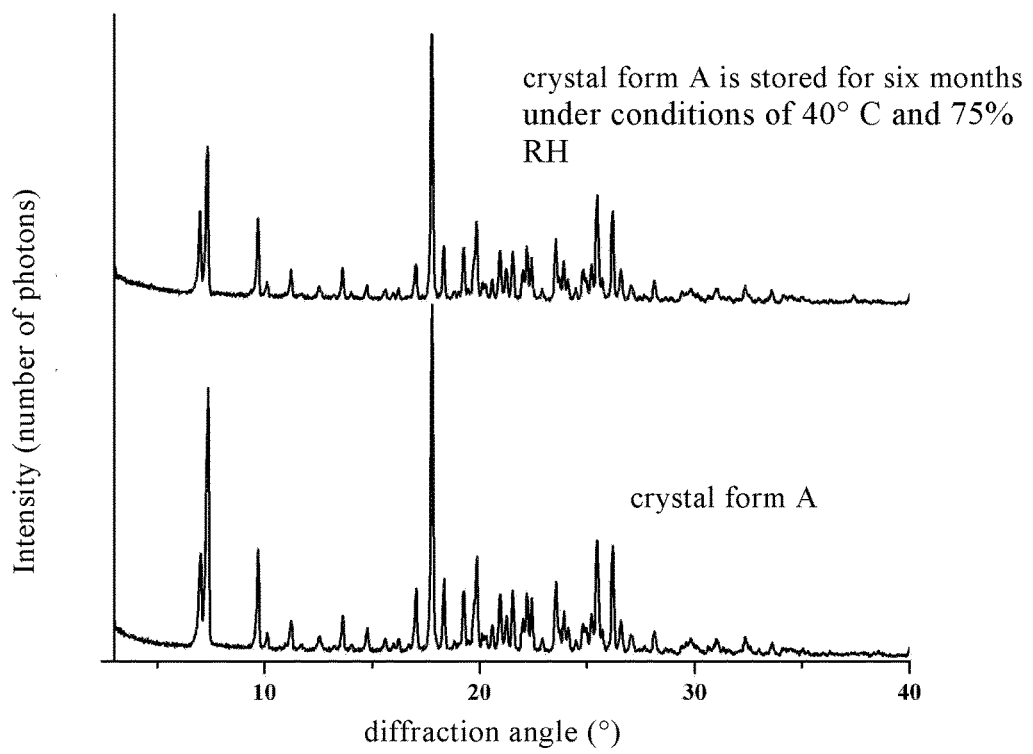
FIG. 5 is an X-ray powder diffraction (XRPD) comparison diagram of crystal form A of inositol nicotinate provided by the present invention stored for half a year at 40° C. and under the condition of 75% of relative humidity.

The crystal form A of inositol nicotinate obtained in the above examples was stored under conditions of 40° C. and 75% RH for six months. The analysis results are shown in FIG. 5. It can be seen from FIG. 5 that its crystal form has not changed, indicating that the crystal form has a good physical stability under high humidity conditions.

The foregoing descriptions are merely preferred embodiments of the present invention, and are not used to limit the present invention. Any modifications, equivalent replacements and improvements made within the spirit and principle of the present invention should be included in the protection scope of the present invention.

The invention claimed is:

1. A crystal form A of inositol nicotinate, wherein X-ray powder diffraction analysis of the crystal form A obtained using Cu-Kα ray measurement, with an error range of ±0.2°, has characteristic diffraction peaks at 7.05, 7.41, 9.74, 17.80, 19.86, 23.57, 25.48 and 26.20 of 2θ value expressed as degrees, with an error range of ±0.2°.

2. The crystal form A of inositol nicotinate of claim 1, wherein the X-ray powder diffraction of crystal form A expressed as 2θ value degrees has characteristic diffraction peaks at diffraction angles of 7.05, 7.41, 9.74, 10.16, 11.26, 12.75, 17.80, 19.86, 20.97, 23.57, 25.48 and 26.20, 26.58, with an error range of ±0.2°.

3. The crystal form A of inositol nicotinate of claim 1, wherein the interplanar spacing d expressed as Å and the relative intensity of the diffraction peak expressed as percentage have the following characteristics:

| 2θ | d | relative intensity % |
|---|---|---|
| 7.05 | 12.53 | 23.4 |
| 7.41 | 11.92 | 46.1 |
| 9.74 | 9.08 | 23.3 |
| 10.16 | 8.70 | 4.3 |
| 11.26 | 7.85 | 8.7 |
| 12.75 | 7.04 | 3.6 |
| 13.66 | 6.48 | 9.2 |
| 17.04 | 5.20 | 12.9 |
| 17.80 | 4.98 | 100 |
| 18.36 | 4.83 | 17.3 |
| 19.28 | 4.60 | 16.2 |
| 19.86 | 4.47 | 24.3 |
| 20.62 | 4.30 | 5.0 |
| 20.97 | 4.23 | 14.9 |
| 21.29 | 4.17 | 8.6 |
| 21.58 | 4.11 | 15.5 |
| 22.03 | 4.03 | 9.0 |
| 22.23 | 3.99 | 16.8 |

-continued

| 2θ | d | relative intensity % |
|---|---|---|
| 22.45 | 3.95 | 12.5 |
| 23.57 | 3.77 | 20.4 |
| 23.93 | 3.71 | 11.0 |
| 25.2 | 3.53 | 11.9 |
| 25.48 | 3.49 | 33.9 |
| 26.20 | 3.40 | 26.1 |
| 26.58 | 3.35 | 9.0. |

4. The crystal form A of inositol nicotinate of claim 1, wherein the X-ray powder diffraction pattern of the crystal form A is essentially as shown in FIG. 1.

5. The crystal form A of inositol nicotinate of claim 1, wherein the crystal form A has one or more characteristics selected from the group consisting of:
   (1) the crystal form A belongs to a monoclinic system, of which the spatial point group is P21/c;
   (2) the unit cell parameters of the crystal form A is: a=12.0470(2) Å, b=17.4688(3) Å, c=18.3057(3) Å; α=γ=90.00°, β=94.5170(10°);
   (3) the unit cell volume of the crystal form A is 3840.41 Å$^3$; and/or
   (4) the crystal density of the crystal form A is 1.4022 g/cm$^3$.

6. The crystal form A of inositol nicotinate of claim 1, wherein the differential scanning calorimetry analysis of crystal form A starts melting at 260° C., and has a maximum endothermic melting peak at 261.14° C.

7. The crystal form A of inositol nicotinate of claim 1, wherein the differential scanning calorimetry pattern of the crystal form A is as essentially shown in FIG. 2.

8. The crystal form A of inositol nicotinate of claim 1, wherein the thermogravimetic analysis pattern of the crystal form A is as essentially shown in FIG. 3.

9. The crystal form A of inositol nicotinate of claim 1, wherein for the thermogravimetic analysis, the crystal form A has a decomposition temperature of 300±1° C., and there is no weight loss peak of crystal water or a binding solvent before the decomposition temperature.

10. The crystal form A of inositol nicotinate of claim 1, wherein the Raman spectrum of the crystal form A has characteristic peaks at 622 cm$^{-1}$, 827 cm$^{-1}$, 903 cm$^{-1}$, 1033 cm$^{-1}$, 1194 cm$^{-1}$, 1276 cm$^{-1}$, 1302 cm$^{-1}$, 1387 cm$^{-1}$, 1592 cm$^{-1}$, 1720 cm$^{-1}$, 1741 cm$^{-1}$, 2971 cm$^{-1}$, and 3067 cm$^{-1}$, with an error range of ±2 cm$^{-1}$.

11. The crystal form A of inositol nicotinate of claim 1, wherein the Raman spectrum of the crystal form A is as essentially shown in FIG. 4.

12. A preparation method of the crystal form A of inositol nicotinate of claim 1, wherein the method is the evaporative crystallization method, the cooling crystallization method or the anti-solvent crystallization method, or a mixed crystallization method comprising at least two of the evaporative crystallization method, the cooling crystallization method and the anti-solvent crystallization method.

13. The method of claim 12, comprising the steps:
   (1) providing a mixture of inositol nicotinate and solvent S, the solvent S is selected from the group consisting of: haloalkane, alcohol, water, and the combinations thereof, and the solid-liquid ratio of the inositol nicotinate and the solvent S is 1 g: 5 mL to 1 g: 15 mL;
   (2) Performing crystallization to obtain the crystal form A of inositol nicotinate.

14. The method of claim 13, wherein
   (a) before the step (2), the method further comprises: heating the mixture to 60-100° C., and optionally, cooling to 0-30° C.; or
   (b) before the step (2), the method further comprises: adding an anti-solvent to the mixture described in step (1) at room temperature; or
   (c) before the step (2), the method further comprises: adding an anti-solvent dropwise to the mixture described in step (1), heating the mixture to 25-70° C. for the evaporation; and/or
   (d) the step (2) further comprises filtering, washing and drying step.

15. The method of claim 12, wherein
   the evaporative crystallization method comprises the following steps: dissolving inositol nicotinate in a mixed solvent of alkyl halide and alcohol, or a mixed solvent of alkyl halide with alcohol in water, and placing at room temperature or heating to volatilize or evaporate the alkyl halide in the system until solid crystals are precipitated, then the solid crystals are filtered, washed and dried; and/or
   the cooling crystallization method comprises the following steps: dissolving inositol nicotinate in a mixed solvent of alkyl halide and alcohol, or a mixed solvent of alkyl halide with alcohol in water, heating to dissolve, and then cooling until solid crystals are precipitated, then the solid crystals are filtered, washed and dried; and/or
   the anti-solvent crystallization method comprises the following steps: dissolving inositol nicotinate in a mixed solvent of alkyl halide with alcohol, or a mixed solvent of alkyl halide with alcohol in water, adding alcohol solvent dropwise at room temperature until solid crystals are precipitated, then the solid crystals are filtered, washed and dried; and/or
   the mixed crystallization method comprises the following steps: dissolving inositol nicotinate in a mixed solvent of alkyl halide and alcohol, or a mixed solvent of alkyl halide with alcohol in water, and evaporating alkyl halide by heating, meanwhile, adding alcohol solvent to the reaction liquid solid until crystals are precipitated, then the solid crystals are filtered, washed and dried.

16. The method according to claim 15, wherein the alkyl halide is one or two or more of chloroform, dichloromethane, or dichloroethane; the alcohol is one or two or more of methanol, ethanol or isopropanol; and/or the alcohol in water is a mixed solvent of one or two or more of methanol, ethanol or isopropanol in water; and/or, in the mixed solvent of alkyl halide and alcohol, the volume ratio of the alkyl halide to the alcohol is 10:1 to 1:10; and/or, the anti-solvent is an alcohol or alcohol water solvent.

17. The crystal form A of inositol nicotinate according to claim 1, prepared according to a method, for use in a medicament and feed, wherein the method is the evaporative crystallization method, the cooling crystallization method or the anti-solvent crystallization method, or a mixed crystallization method comprising at least two of the evaporative crystallization method, the cooling crystallization method and the anti-solvent crystallization method.

* * * * *